United States Patent [19]

Nillesen

[11] Patent Number: 4,574,307

[45] Date of Patent: Mar. 4, 1986

[54] LINE SYNCHRONIZING CIRCUIT FOR A PICTURE DISPLAY DEVICE

[75] Inventor: Antonius H. H. J. Nillesen, Eindhoven, Netherlands

[73] Assignee: U.S. Philips Corporation, New York, N.Y.

[21] Appl. No.: 529,893

[22] Filed: Sep. 7, 1983

[30] Foreign Application Priority Data

Sep. 14, 1982 [NL] Netherlands .......................... 8203556

[51] Int. Cl.[4] ............................ H03L 7/00; H04N 5/04
[52] U.S. Cl. ..................................... 358/158; 358/148; 358/159; 358/17; 331/18; 331/20; 328/133
[58] Field of Search ................................ 358/148–159, 358/17; 331/20, 18, 17; 328/133, 181, 187

[56] References Cited

U.S. PATENT DOCUMENTS 4,214,260  7/1980  van Straaten ........................ 358/148

Primary Examiner—Tommy P. Chin
Assistant Examiner—Michael D. Parker
Attorney, Agent, or Firm—Thomas A. Briody; William J. Streeter; Edward W. Goodman

[57] ABSTRACT

A line synchronizing circuit for a picture display device comprising a control loop for controlling a line oscillator. An incoming line synchronizing signal and also a reference signal generated by the oscillator are applied to a phase discriminator circuit. The output signal of the phase discriminator circuit is smoothed to obtain the control voltage for the oscillator. Pull-in of the control loop is established by means of a coincidence detector. Prior to that, an edge of the reference signal is compared with the center instant of a line synchronizing pulse. When the control loop is in the pulled-in state, it is changed by the coincidence detector to compare the leading edge of a line synchronizing pulse to the center instant between the said edge of the reference signal and its first preceding edge.

9 Claims, 5 Drawing Figures

LINE SYNCHRONIZING CIRCUIT FOR A PICTURE DISPLAY DEVICE

BACKGROUND OF THE INVENTION

The invention relates to a line synchronizing circuit for a picture display device, comprising a control loop for controlling the frequency and/or the phase of a line oscillator, having means for applying an incoming pulse-shaped line synchronizing signal and a reference signal generated by the oscillator to a phase discriminator for determining the phase difference between the signals applied thereto and having a loop filter for smoothing the phase discriminator output signal and for applying the smoothed control signal obtained to the oscillator for the control thereof, said control loop being such that during operation, in the target state thereof, the centre instant of an edge of the reference signal substantially coincides with the center instant between a leading edge and the subsequent trailing edge of a line synchronizing pulse, the line synchronizing circuit also comprising a coincidence detector for detecting a phase difference between an incoming line synchronizing pulse and an oscillator pulse which difference is less than a predetermined value and for changing over the mode of operation of the control loop.

Such a line synchronizing circuit is disclosed in U.S. Pat. No. 4,214,260. In this known circuit, a number of change-over operations are effected by means of the coincidence detector for accellerating pull-in of the control loop when there is no coincidence and for increasing the noise insensitivity when there is coincidence, that is to say in the pulled-in state.

Line synchronizing circuits which, as the circuit mentioned above, control at the center instant of the line synchronizing pulses, have the disadvantage that a phase error occurs at the commencement of the field period, which error is caused by the fact that the duration of the synchronizing pulses occurring during the field blanking period is, different from the duration of the line synchronizing pulses occurring during the field trace period. As a result thereof, the content of the phase discriminator output signal differs from its target value, which results in an error in the control which has not yet been corrected at the end of the field blanking period. As a result thereof, vertical lines are displayed as curved lines at the top of the picture display screen. This error can be corrected, several methods to do so are known. It is, for example, possible to render the control loop inoperative during the field blanking period. This has however the disadvantage that pull-in is delayed.

SUMMARY OF THE INVENTION

The invention has for its object to provide a circuit of the above-mentioned type, in which the error is prevented while a rapid pull-in of the control loop is ensured. According to the invention, the line synchronizing circuit is characterized in that the control loop is arranged such that in its target state, after the change-over action by means of the coincidence detector, the center instant of the leading edge of an incoming line synchronizing pulse substantially coincides with the center instant between the edge of the reference signal and its first preceding edge.

The invention is based on the recognition that the phase error produced during the field blanking interval can be prevented from occurring if the control is not effected to the center instant but to the leading edge of the line synchronizing pulse, as in that case, the duration of the pulse is of no importance. In other words, the leading edge of the line synchronizing pulse contains the information required for the control loop. Measures must indeed be taken to ensure that the trailing edge of this pulse does not influence the control, which means that the reference pulse should not be too long and consequently that the period of time in which the comparatively short pulses coincide during the pulling-in procedure is very short compared to the periods of the signals applied to the phase discriminator. This results in the output signal of the phase discriminator in the open loop state is not symmetrical over one period of the difference frequency, in spite of the fact that all the phase positions between 0° and 360° are passed through and consequently that the generated control voltage has an incorrect value, which, in the closed loop state, causes an incorrect frequency of the oscillator signal.

This disadvantage is obviated if the line synchronizing pulses applied to the phase discriminator are given a longer duration in the period, for example, a symmetrical square-wave shape. However, this requires a regenerator circuit for deriving such a square-wave signal from the incoming line synchronizing signal, which regenerator must comprise a plurality of precise and consequently costly timing elements.

The invention proposes a different measure. First, a control is effected in known manner to the center of the line synchronizing pulse, causing pull-in to be effected rapidly. Thereafter the circuit is changed-over to a control on the leading edge of the line synchronizing pulse, which control may be considered as a fine control, it not being possible that the fact that the control loop now has a poor pull-in behavior has a negative effect on the pull-in state since this state has already occurred.

Preferably, the line synchronizing circuit according to the invention is characterized in that after change-over by means of the coincidence detector, the duration of the reference pulse formed by the edges is approximately equal to the duration of the line synchronizing pulse. Because of this measure an, otherwise small, phase shift does not occur.

In a preferred embodiment the line synchronizing circuit in accordance with the invention, is characterized in that the phase discriminator is in the form of a controllable switch which prior to change-over by means of the coincidence detector is operated by the line synchronizing signal for conveying the reference signal to the loop filter and which after the said change-over action is operated by the reference pulse for conveying the line synchronizing signal to the loop filter.

DESCRIPTION OF THE DRAWINGS

The invention will now be further described by way of example with reference to the accompanying Figures, in which.

DESCRIPTION OF THE PREFERRED EMBODIMENTS

Figures 1, 2:
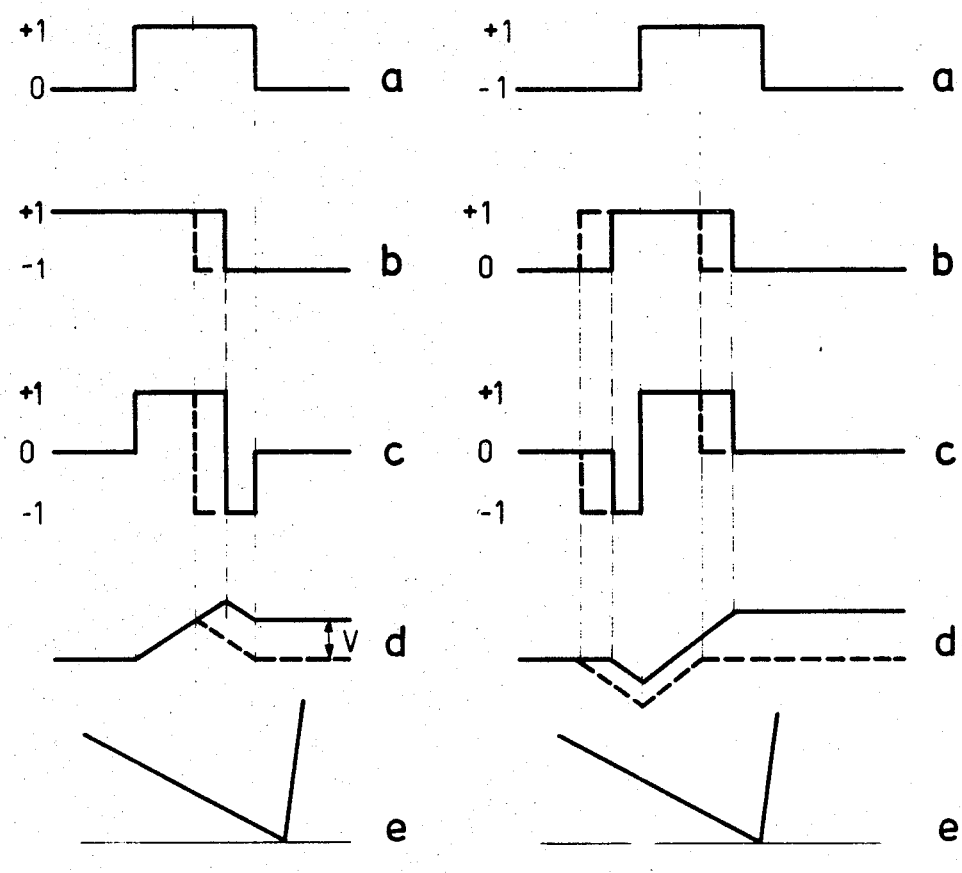
FIG. 1 shows waveforms produced in the circuit in accordance with the invention, prior to the change-over operation.
FIG. 2 shows waveforms produced therein after the change-over operation.

In FIG. 1a a line synchronizing pulse is shown which is applied to a phase discriminator in a phase control loop. During the major portion of the line period the signal level has a low value, denoted by 0, and during the remaining portion it assumes a high value, denoted by +1. The phase discriminator is also supplied with a reference signal shown in FIG. 1b and coming from a line oscillator, which signal assumes a value −1 or a value +1. The phase discriminator multiples these two signals by each other, FIG. 1c shows the result. The signal shown in FIG. 1c is integrated by a low-pass filter to provide the control voltage (FIG. 1d) for the oscillator.

The control loop is arranged such that in the target state thereof, an edge of the reference signal shown in FIG. 1b is produced at the center instant of the pulse shown in FIG. 1a. The waveforms shown in FIGS. 1a to d, inclusive, show the case in which the frequency of the oscillator is below the target value thereof. A transition from +1 to −1 in the reference signal then occurs after the center instant. The target position of this transition is indicated by means of a broken line. The phase discriminator output signal has the value 0 when the pulse shown in FIG. 1a does not occur and when this pulse occurs, the output signal has first the value +1 and thereafter the value −1, the transition produced coinciding with the transition shown in FIG. 1b. From FIG. 1d, it can be seen that the generated control voltage has a positive value V compared with its nominal value. In response to voltage V, the frequency of the oscillator is increased, as a result of which the edge in FIG. 1b is advanced. When the edge has reached its target position, the deviation of the control voltage relative to the nominal value thereof becomes zero, which is the target state in which the oscillator is not readjusted and has the same frequency as the line synchronizing pulses and a fixed phase relationship therewith. In the said target state, the waveforms shown in FIGS. 1c and d are symmetrical relative to the center instant of the pulse shown in FIG. 1a. If originally the frequency of the oscillator exceeds the line frequency, then the falling edge of the reference pulse is first produced prior to this instant and the regenerated control voltage is negative relative to its nominal value. FIG. 1b does not show the position of the rising edge of the reference signal, it will be obvious that the pulse this edge forms with the falling edge must not be narrower than the synchronizing pulse. Otherwise the control voltage might depend on the position of the rising edge, which would introduce an ambiguity in the control.

The above-described operation of a control loop controlling to the center instant of the line synchronizing pulse and the means therefore are of a known type. The line synchronizing circuit of which the control loop forms part, also comprises a coincidence detector which detects in known manner that coincidence has occurred once or a predetermined number of times, i.e. the, at least partly, simultaneous occurrence of an incoming line synchronizing pulse and a short gate pulse generated by the oscillator. The coincidence detector may alternatively be in the form of an auxiliary phase discriminator for determining that the difference between the position of the falling edge of the signal shown in FIG. 1b and the target position thereof is less than a predetermined value. By means of the coincidence detector, a number of elements of the circuit can be changed-over when there is coincidence, that is to say, in the pulled-in state of the control loop. In this way, it is accomplished that the control loop has a fast response to phase changes in the non-synchronized state and a slow and noise insensitive response in the synchronized state.

In accordance with the invention, the synchronizing circuit is switched over in such a way by the coincidence detector, after the final state of the control loop of FIG. 1 has been obtained, that the variation shown in FIG. 2 occurs. FIG. 2a also shows the line synchronizing pulse, its signal level varying between the values −1 and +1. FIG. 2b shows the reference signal having a level of either 0, or +1. These values indicate that the input signals of the phase discriminator of FIG. 2 are, as it were, interchanged relative to the case shown in FIG. 1 as regards the interpretation of "high" and "low". FIG. 2c shows the output signal of the phase discriminator while FIG. 2d also shows the result of the integration of this signal for obtaining a control voltage for the oscillator.

In the target state of the control loop of FIG. 2, the leading edge of the line synchronizing pulse of FIG. 2a occurs at the center instant of the reference pulse shown in FIG. 2b. This is illustrated in FIGS. 2b, c and d by means of broken lines. Thanks to this control mode, no phase error occurs during the field blanking period, as the width of the synchronizing pulse is of no importance. FIG. 2 shows again the case in which the reference signal occurs too late relative to the target position thereof. The period of time between the occurrence of the leading edge of the reference pulse and the occurrence of the leading edge of the synchronizing pulse is consequently shorter than the period of time between the occurrence of the last-mentioned leading edge and the occurrence of the trailing edge of the reference pulse. FIG. 2c shows that the result of the multiplication of the signals shown in FIGS. 2a and b has the value +1 for a longer period of time, more specifically after the transition which corresponds to the leading edge of the synchronizing pulse, than the value −1 it has prior to this transition. For these circumstances, it can be seen from FIG. 2d that the resultant control voltage is posive relative to its nominal value. In response to this voltage, the frequency of the oscillator is increased, as a result of which the pulse of FIG. 2b is advanced. Thereafter the control voltage assumes its nominal value, the frequency of the oscillator not being readjusted anymore, at the instant that the leading edge of the synchronizing pulse coincides with the center of the reference pulse. In this situation the waveforms of FIGS. 2c and d are symmetrical relative to the center instant of the pulse shown in FIG. 2b. If the reference signal occurs too early relative to its target position, then the generated control voltage is negative relative to its nominal value and the pulse of FIG. 2b is shifted back until the symmetry is obtained.

It is a condition that the duration of the reference pulse should not exceed the duration of the line synchronizing pulse. Otherwise, the trailing edge of the synchronizing pulse might occur before the end of the reference pulse, so that the generated control voltage might also depend on the position of the trailing edge.

For a person skilled in the art it will, however, be obvious that the reference pulse must not be too short in view of the influence of its duration on the loop gain. It should be noted that when the target position of the control loop of FIG. 1 is reached, this position will generally be treated by the control loop of FIG. 2 as an error which needs correction. This results in the above mentioned, slight shift for the oscillator and for the signals derived therefrom. This shift does not occur, which ensures improved operation of the coincidence detector, particularly in the absence of much noise in the incoming signal, if the reference pulse has substantially the same duration as the line synchronizing pulse. In that case, the waveforms have the same positions in the final state of the control loop of FIG. 2 as in the final state of the control loop of FIG. 1. This can be seen from FIG. 2 in which the pulses of FIG. 2a and b have the same duration, the leading edge of the pulse of FIG. 2a coinciding in the target state with the center of the pulse shown in FIG. 2b, while the traililng edge of that pulse shown in FIG. 2b coincides with the center of the pulse shown in FIG. 2a.

It should be noted that the description of the control loop with reference to FIGS. 1 and 2 is always based on the ideal case of an infinite loop gain. In actual practice there will, however, always be a small phase error relative to the target value, which results in a control voltage which is not equal to the nominal value. Because of the short duration of the pulses applied to the phase discriminator compared with the line period, the pull-in behavior of the control loop of FIG. 2 is poor. On account of the fact that this loop must process small phase variations after coincidence has been detected, that is to say after the control loop shown in FIG. 1 has already been pulled in, this poor behavior is not objectionable. If so large a deviation occurs that the loop is not capable of pulling in, then the coincidence detector effects a switch to the control loop of FIG. 1, whereafter the above-described procedure is repeated. It will be obvious that the control loop of FIG. 1 must indeed have a good pull-in behavior. This is the case if the duration of the reference pulse in FIG. 1b is not short relative to the line period. The optimum pull-in behavior is obtained with a symmetrical, for example squarewave, waveform, that is to say if the rising edge of the signal of FIG. 1b occurs approximately 32 μs before the falling edge shown, as the line period has a duration of approximately 64 μs (European and American television standards).

Figure 3:
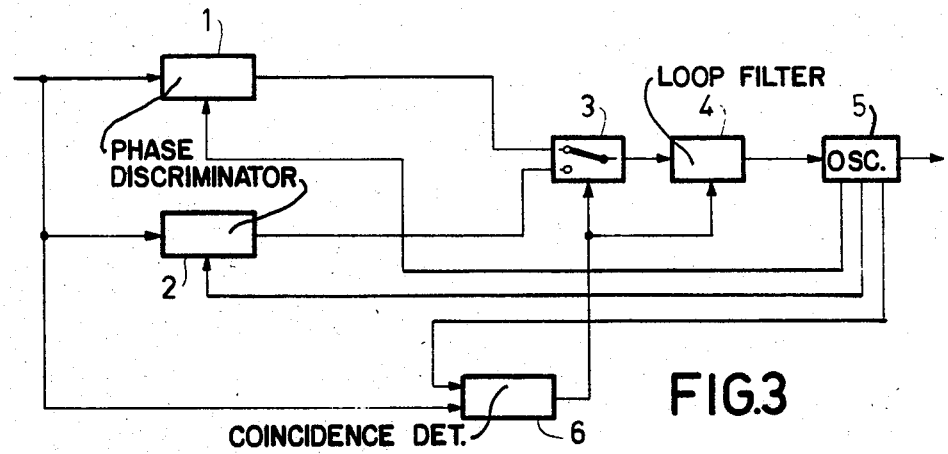
FIG. 3 shows a first embodiment of the circuit in accordance with the invention.

FIG. 3 shows a line synchronizing circuit comprising two phase discriminators 1 and 2, to which a incoming line synchronizing signal is applied. The output signals are applied via a change-over switch 3 to a loop filter 4, whose output voltage is the control voltage for a line oscillator 5. The signal generated by oscillator 5 is further processed in known manner for line (horizontal) deflection in a picture display device of which the present circuit forms part. Oscillator 5 also generates other line-frequency signals which are applied to phase discriminators 1 and 2 and also to a coincidence detector 6. Detector 6 also receives the incoming line synchronizing pulses and operates change-over switch 3.

Phase discriminators 1 and 2 may be considered as multiplying stages for the input signals of these discriminators. Both discriminators are preceded by clamping circuits, not shown, for clamping the signal levels of each input signal. The square-wave reference signal of FIG. 1b, which signal is preferably symmetrical, and also the line synchronizing signal of FIG. 1a are applied to phase discriminator 1. By means of the above-mentioned clamping circuits, it is ensured that both levels of the reference signal have fixed values while the low level, located between the pulses, of the synchronizing signal has a value which is located equidistantly between the levels of the reference signal. In these circumstances, the output signal of discriminator 1 is the signal shown in FIG. 1c and is applied, via change-over switch 3, to filter 4 for controlling oscillator 5 as long as this oscillator does not have the proper frequency and phase.

In a similar manner the two levels of the line synchronizing signal (FIG. 2a) applied to phase discriminator 2 have fixed values, while, the low level between the pulses of the reference signal shown in FIG. 2b is clamped on the average value of these levels. Multiplying these signals results in the signal shown in FIG. 2c, which is applied to filter 4 via change-over switch 3 as soon as coincidence between the input signals of detector 6 has been detected. Also filter 4 can be changed-over by detector 6, more specifically to a higher value of its time constant, which increases the noise insensitivity of the synchronizing circuit.

Figure 4:
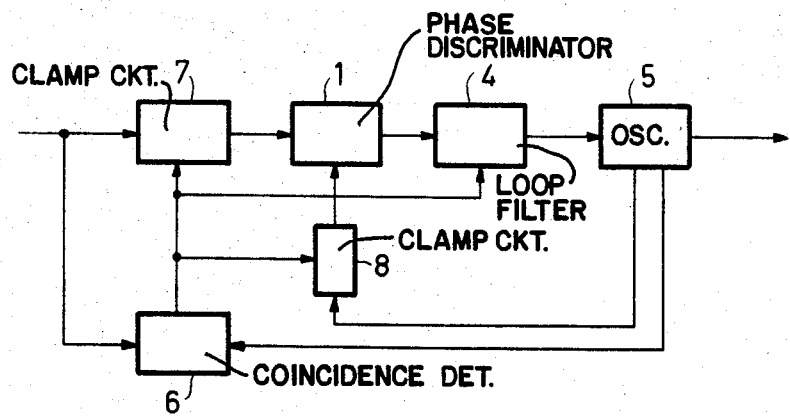
FIG. 4 shows a second embodiment of the circuit in accordance with the invention.

FIG. 4 shows a line synchronizing circuit comprising only one phase discriminator 1. Both inputs of this discriminator are preceded by a clamping circuit 7 and 8, respectively, and no change-over switch is provided between phase discriminator 1 and filter 4. The clamping circuits 7 and 8 are changed-over by means of coincidence detector 6. When the control loop is in the non-pulled-in state, the two input signals of phase discriminator 1 are clamped in FIG. 4 in the same manner as the input signals of phase discriminator 1 in FIG. 3. At the instant coincidence is detected, the time constant of filter 4 is adjusted to a higher value, while the input signals of phase discriminators 1 are clamped, in FIG. 4, in the same manner as the input signals of phase discriminator 2 are clamped in FIG. 3.

Figure 5:
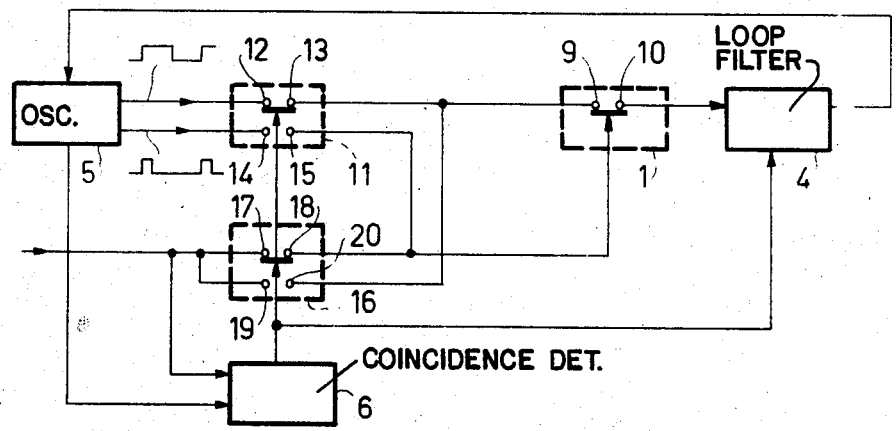
FIG. 5 shows a third embodiment of the circuit in accordance with the invention.

The embodiment of FIG. 5 does not require clamping circuits. Phase discriminator 1 is in the form of a controllable switch having two terminals 9 and 10, which are interconnectable for conveying a signal to filter 4. A switch 11 has four terminals 12, 13, 14 and 15, while a switch 16 has four terminals 17, 18, 19 and 20. Terminal 12 is connected to an output of oscillator 5 at which a symmetrical square-wave signal is present. Terminal 14 is connected to an output of oscillator 5 at which a pulse-shaped signal is present, the pulses having substantially the same duration as the incoming line synchronizing pulses. Terminals 17 and 19 are connected to the input of the incoming line synchronizing pulses. Terminals 13 and 20 are connected to terminal 9, while terminals 15 and 18 are interconnected, the signal on the connection formed operating switch 1. By means of coincidence detector 6 either terminals 12 and 13, on the one hand, and terminals 17 and 18, on the other hand, or terminals 14 and 15, on the one hand, and terminals 19 and 20, on the other hand, can be interconnected. The first case is shown in FIG. 5 and occurs when there is no coincidence, while the second case occurs in the event of coincidence. If there is no coincidence, the square-wave signal from oscillator 5 is conveyed to filter 4 via terminals 9 and 10 during the occurrence of a line synchronizing pulse. This is the situation shown in FIG. 1. If there is coincidence, switch 1 is operated by the reference signal shown in FIG. 2b. During the occurrence thereof, the line synchronizing signal is conveyed to filter 4 via terminals 9 and 10. This is the situation shown in FIG. 2. The value 0 for the signals shown in FIGS. 1 and 2, respectively, is the result of the fact that switch 1 is open, while the input signals are high or low, respectively.

In the example shown in FIG. 5, it is advantageous to construct oscillator 5 in known manner as a sawtooth generator, for example a generator in which a capacitor is successively charged and discharged by means of current sources and/or resistors. The required pulse-shaped signals are derived from the generated sawtooth voltage. FIG. 1e and 2e, respectively, show the sawtooth. At the instant the descending portion of the sawtooth reaches a low d.c. voltage level, the ascending portion is initiated, for example by changing-over the current sources. This said level is derived from the control voltage generated by filter 4. If in response to this control this level assumes a higher value, then the period of the sawtooth generator becomes shorter and consequently the frequency becomes higher. From FIGS. 1d and 1e, it can be seen that the operation of the sawtooth generator can be disturbed by the value of the voltage from filter 4 during the occurrence of the pulses shown in FIG. 1, as this voltage is subjected to a temporary increase, which may cause a premature initiation of the ascending portion of the sawtooth. This disturbance will not occur if the time constant of filter 4 is large. As the control loop of FIG. 1 must be capable of a fast response, this means that a compromise must be found. From FIGS. 2d and e it can be seen that such a compromise is not necessary after the control shown in FIG. 2 has been changed-over, as the voltage of FIG. 4 is submitted to a temperary decrease during the occurrence of the pulses shown in FIG. 2, so that no disturbance need be feared.

In the circuit disclosed in U.S. Pat. No. 4,214,260 a gate pulse, produced by the line oscillator and being somewhat wider than a line synchronizing pulse, becomes operative after changeover by means of the coincidence detector. The phase discriminator is keyed by this gate pulse in the synchronized state so as to reduce the influence of noise and disturbances. If now an edge of the line synchronizing pulse disappears beyond this window, for example due to a phase shift in a pick-up device, then the phase discriminator receives information via only one edge, which considerably reduces the loop gain compared to the original value. If, for example, the gate pulse exceeds the synchronizing pulse by 1 $\mu$s then this error occurs already at a shift of 0.5 $\mu$s. A wider gate pulse would have a less critical duration, but this would have a negative effect on the noise behavior. Because of the operation of the control loop, described with reference to FIG. 2, it is not necessary to generate a separate gate pulse in the circuit in accordance with the invention. As above, the reference pulse may have a duration which is equal to the duration of the synchronizing pulse, i.e. approximately 5 $\mu$s, a phase deviation relative to the nominal position of not more than half the duration of this pulse, i.e. approximately 2.5 $\mu$s, not having a negative effect on the loop gain.

In prior art line synchronizing circuits a compromise must be sought as regards the value of the time constant of the loop filter, as this value must be low so as to reduce to some extent the phase error which is still present at the end of the field blanking period. On the other hand, this value must be high in view of the noise suppression. Thanks to the measure in accordance with the invention, the phase error need no longer be taken into account. In certain circumstances the changeover of the time constant may even be omitted.

In the foregoing, the signals are always described as being pulse-shaped or square-wave signals. It should be noted that these shapes, at least as regards the reference signal, are not necessary. The signal shown in FIG. 1b must indeed have the value 0 in the target state at the center instant of the pulse shown in FIG. 1a, that is to say the average value of the levels of this pulse, and it must have the value +1 and −1, respectively, some time prior to the center instant and the same length of time thereafter. So it must be antisymmetrical relative to the said instant. For this purpose a sine wave is alternatively suitable, and also a sawtooth or a triangular shape. In a similar manner, the square wave pulse shown in FIG. 2b may be replaced by any shape which is symmetrical relative to the center instant thereof, for example a triangular shape having the vertex at this instant, or a cosine-shape or keyed retrace pulse. The active duration of the pulse must indeed satisfy the above-mentioned condition, so that the trailing edge of the line synchronizing pulse does not influence the control. As a matter of fact, there are, in actual practice, no square-wave signals whose edges have an infinitely short duration, so that in all cases, it is more appropriate to speak of the center instants of the edges.

What is claimed is:

1. A line synchronizing circuit for a picture display device, comprising a control loop for controlling the frequency and/or the phase of a line oscillator, having means for applying an incoming pulse-shaped line synchronizing signal and a reference signal generated by the oscillator to a phase discriminator circuit for determining the phase difference between the signals applied thereto and having a loop filter for smoothing the phase discriminator output signal and for applying the smoothed phase discriminator output signal as a control signal, to the oscillator for the control thereof, said control loop being such that during operation, in a target state thereof, the center instant of an edge of the reference signal substantially coincides with the center instant between a leading edge and the subsequent trailing edge of a line synchronizing pulse, the line synchronizing circuit also comprising a coincidence detector for detecting a phase difference between an incoming line synchronizing pulse and an oscillator pulse of said line oscillator which difference is less than a predetermined value and for changing-over the mode of operation of the control loop, characterized in that said line synchronizing circuit further comprises means coupled to said phase discriminator circuit for changing the operation thereof in response to said coincidence detector, whereby, when coincidence is detected, said phase discriminator circuit controls said line oscillator so that the center instant of the leading edge of an incoming line synchronizing pulse substantially coincides with the center instant between said edge of the reference signal and a first preceding edge thereof.

2. A line synchronizing circuit as claimed in claim 1, characterized in that after change-over by said changing means in response to the coincidence detector detecting coincidence, the duration of the reference pulse defined by said edges is approximately equal to or shorter than the duration of the line synchronizing pulse.

3. A line synchronizing circuit as claimed in claim 1, characterized in that after change-over by said changing means in response to the coincidence detector detecting coincidence, the duration of the reference pulse defined by said edges is approximately equal to the duration of the line synchronizing pulse.

4. A line synchronizing circuit as claimed in claim 1, characterized in that prior to coincidence being detected by said coincidence detector and change-over by said changing means in response thereto, the reference signal has a symmetrical shape.

5. A line synchronizing circuit as claimed in claim 1, 2, 3 or 4, characterized in that said phase discriminator circuit comprises a first and a second phase discriminator in which said second phase discriminator is operative after change-over by said changing means in response to the coincidence detector detecting coincidence, while the first phase discriminator is operative prior to this change-over.

6. A line synchronizing circuit as claimed in claim 5, characterized in that the control loop comprises clamping circuits for clamping the signal levels of the first and second phase discriminator input signals, the signal level between the line synchronizing pulses applied to the first phase discriminator being clamped to the average value of the level of the reference signal also applied to the first phase discriminator, while the signal level between pulses of the reference signal applied to the second phase discriminator is clamped to the average value of the levels of the line synchronizing signal also applied to the second phase discriminator.

7. A line synchronizing circuit as claimed in claim 1, 2, 3 or 4, characterized in that the control loop comprises a clamping circuit for clamping the signal level of the phase discriminator circuit input signals, the signal level between the line synchronizing pulses being clamped, prior to change-over by said changing means in response to the coincidence detector detecting coincidence, to the average value of the levels of the reference signal, while after change-over by said changing means, the signal level between the pulses of the reference signal is clamped to the average value of the levels of the line synchronizing signal.

8. A line synchronizing circuit as claimed in claim 1, 2, 3 or 4, characterized in that the phase discriminator circuit comprises a controllable switch which, prior to change-over by said changing means is operated by the line synchronizing signal for conveying the reference signal to the loop filter and which, after change-over by said changing means is operated by the reference pulse for conveying the line synchronizing signal to the loop filter.

9. A line synchronizing circuit as claimed in claim 1, characterized in that the line oscillator comprises a sawtooth generator having a change-over point on reaching a d.c. voltage level controlled by the control loop, the change in voltage of the control signal applied to the oscillator being, during the occurrence of the line synchronizing pulses after change-over of the phase discrimination circuit by said changing means in response to the coincidence detector detecting coincidence, opposite to the change in the generated sawtooth relative to said d.c. voltage level during said occurrence.

* * * * *